United States Patent
Srivari et al.

(10) Patent No.: US 12,172,944 B2
(45) Date of Patent: Dec. 24, 2024

(54) PROCESS FOR THE PREPARATION OF TAPENTADOL AND ANALOGS THEREOF

(71) Applicant: COUNCIL OF SCIENTIFIC AND INDUSTRIAL RESEARCH, New Delhi (IN)

(72) Inventors: Chandrasekhar Srivari, Hyderabad (IN); Satyendra Mainkar Prathama, Hyderabad (IN); Kranthi Kumar Ramagonolla, Hyderabad (IN); Sukumar Genji, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 609 days.

(21) Appl. No.: 17/598,105

(22) PCT Filed: Mar. 12, 2020

(86) PCT No.: PCT/IN2020/050228
§ 371 (c)(1),
(2) Date: Sep. 24, 2021

(87) PCT Pub. No.: WO2020/194326
PCT Pub. Date: Oct. 1, 2020

(65) Prior Publication Data
US 2022/0177413 A1    Jun. 9, 2022

(30) Foreign Application Priority Data
Mar. 28, 2019   (IN) .............................. 201911012128

(51) Int. Cl.
*C07C 213/08*   (2006.01)
*C07C 213/00*   (2006.01)
*C07D 335/02*   (2006.01)

(52) U.S. Cl.
CPC .......... *C07C 213/08* (2013.01); *C07C 213/00* (2013.01); *C07D 335/02* (2013.01)

(58) Field of Classification Search
CPC ............................ C07C 213/08; C07D 335/02
See application file for complete search history.

(56) References Cited

U.S. PATENT DOCUMENTS 8,440,863 B2 * 5/2013 Filliers .................. C07C 213/08
                                                                564/443
8,853,456 B2 * 10/2014 Rajadhyaksha ....... C07C 213/00
                                                                564/336

FOREIGN PATENT DOCUMENTS

EP          0693475        7/1995
WO    WO 2004108685      12/2004
(Continued)

OTHER PUBLICATIONS

Ward, D.E., The thiopyran route to polypropionates, Chemical Communications, 47(41), p. 11275-11393 (Year: 2011).*
(Continued)

*Primary Examiner* — Yate' K Cutliff
(74) *Attorney, Agent, or Firm* — Norton Rose Fulbright US LLP

(57) ABSTRACT

The present invention relates to a process for the preparation of tapentadol and analogs or compounds or stereoisomers of formula (I), Formula I wherein, A is aryl, heteroaryl, and cycloalkyl; R is H, OH, OR$^1$, halogen, $C_1$-$C_{12}$ alkyl, cycloalkyl, aryl or heteroaryl; R$^1$ is $C_1$-$C_{12}$ alkyl, cycloalkyl, aryl or heteroaryl, wherein each of these groups may further be substituted with one or more substituent selected from H, OH, halogen, CN, $NO_2$, $C_1$-$C_4$ alkyl or phenyl. Further, the multi-step process involves no column chromatography purification until the very last step. This makes this process highly commercially viable and industrially useful.

(Continued)

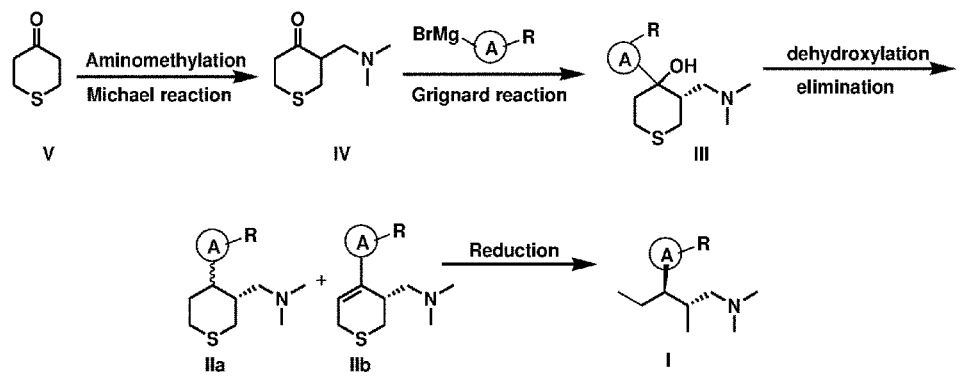

Schematic flowchart for the preparation of analogs of formula (I)

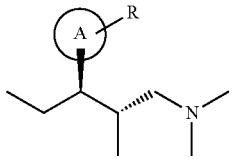

Formula I

10 Claims, 2 Drawing Sheets

(56) References Cited

FOREIGN PATENT DOCUMENTS

| WO | WO 2008012046 | 1/2008 | | |
|---|---|---|---|---|
| WO | WO 2008012047 | 1/2008 | | |
| WO | WO 2013105109 | 7/2013 | | |
| WO | WO-2013105109 A1 * | 7/2013 | ........... | C07C 213/08 |

OTHER PUBLICATIONS

Kranthikumar, R., et al., tetrahydrothiopryan-4-one as five-carbonsource for scalable synthesis of ()-tapentadol, Organic Process Research & Development, vol. 23, No. 7, Jun. 26, 2019, pp. 1369-1373 (Year: 2019).*

Urban, J., et al., 4-aryl-3-(dimethylaminomethyl) thiacyclohexane-4-ols including the thia analogue of tramadol; synthesis and analgetic activity, Collection Czechoslovak Chem. Commun., vol. 52, No. 5, pp. 1340-1351 (Year: 1987).*

Ward, D.E. "The Thiopyran Route to Polypropionates", Chemical Communications, 2011, 47 (41), 11375-11393.

International Search Report issued in corresponding PCT Application No. PCT/ IN2020/050228 dated Mar. 12, 2020.

* cited by examiner

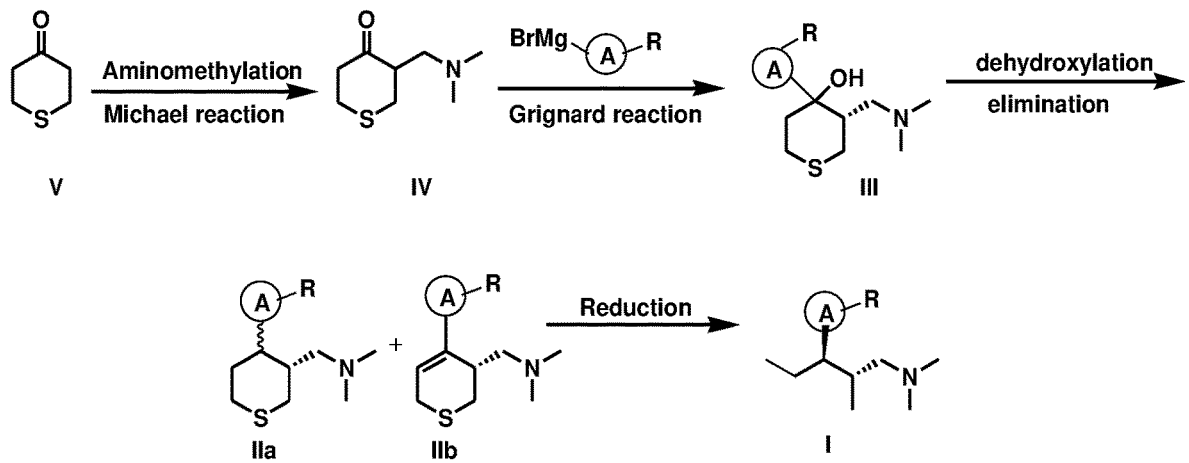
Figure 1: Schematic flowchart for the preparation of analogs of formula (I)
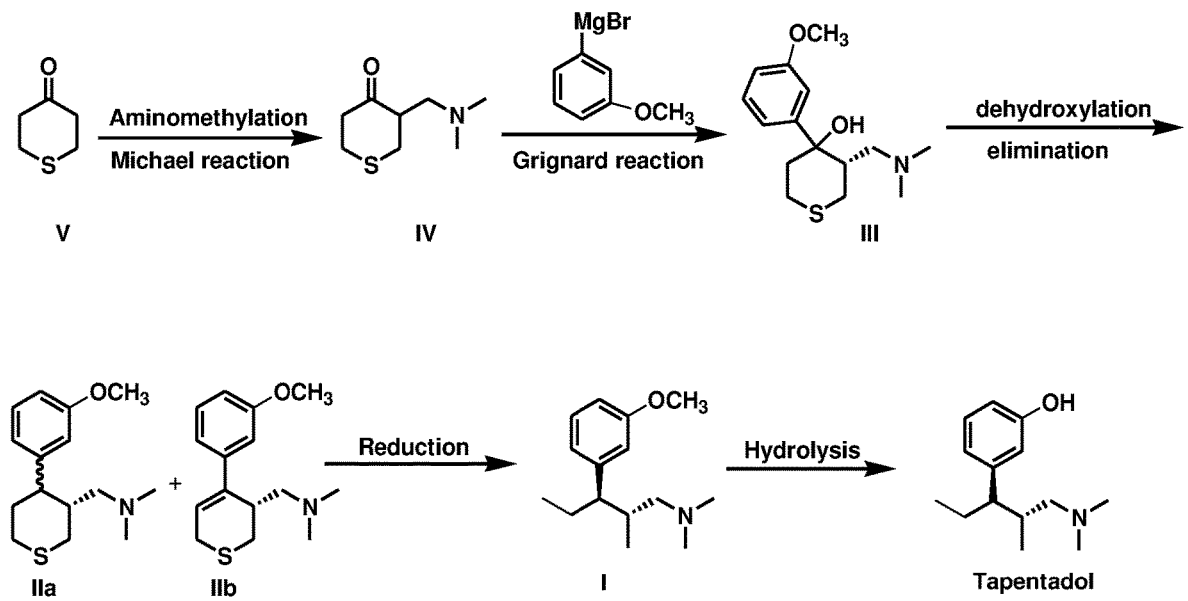
Figure 2: Schematic flowchart for the synthesis of tapentadol

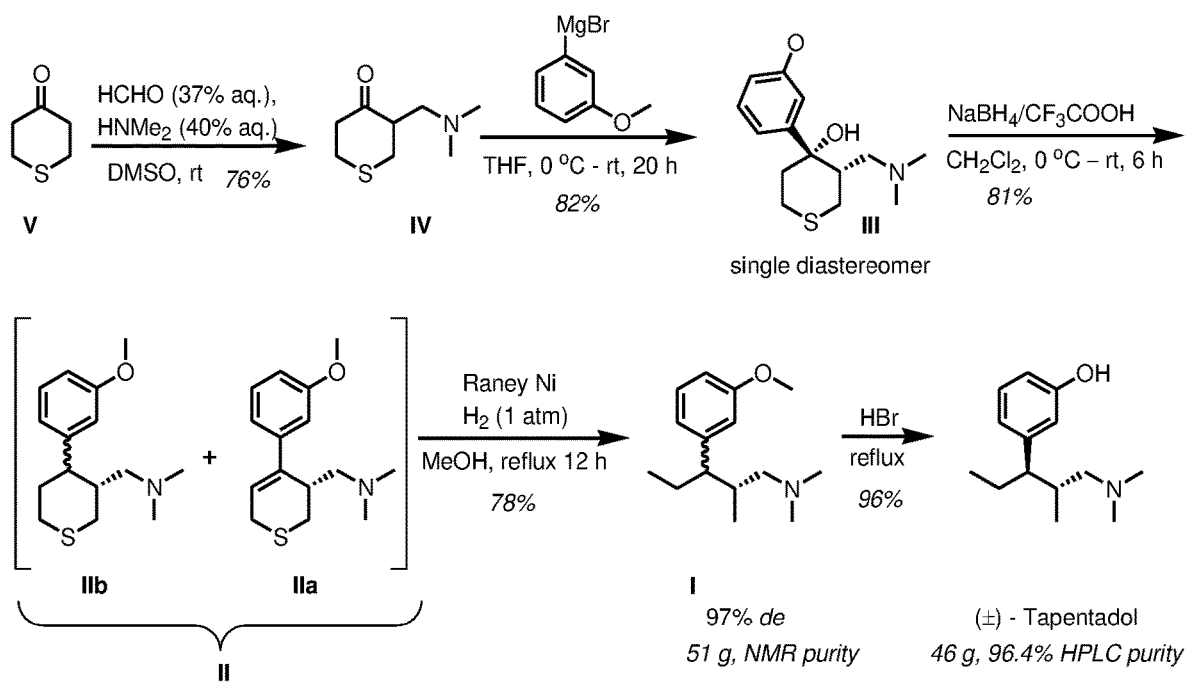
Figure 3: Schematic flowchart for the synthesis of tapentadol along with the reaction conditions

PROCESS FOR THE PREPARATION OF TAPENTADOL AND ANALOGS THEREOF

CROSS-REFERENCE TO RELATED APPLICATIONS

This application is a national phase application under 35 U.S.C. § 371 of International Application No. PCT/IN2020/050228 filed 12 Mar. 2020, which claims priority to Indian patent application No. 201911012128 filed 28 Mar. 2019. The entire contents of each of the above-referenced disclosures is specifically incorporated herein by reference without disclaimer.

FIELD OF THE INVENTION

The present invention relates to a process for the preparation of tapentadol and analogs of formula I from tetrahydro-4H-thiopyranone,

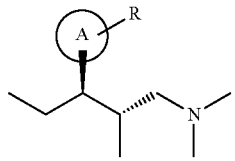

Formula I wherein, A is aryl, heteroaryl, and cycloalkyl; R is H, OH, $OR^1$, halogen, $C_1$-$C_{12}$ alkyl, cycloalkyl, aryl or heteroaryl; $R^1$ is $C_1$-$C_{12}$ alkyl, cycloalkyl, aryl or heteroaryl, wherein each of these groups may further be substituted with one or more substituent selected from H, OH, halogen, CN, $NO_2$, $C_1$-$C_4$ alkyl or phenyl.

BACKGROUND OF THE INVENTION

Pain management using analgesics is a well-studied therapeutic area. Development of molecules targeting different therapeutic classes, such as anticonvulsants, antidepressants, local anaesthetics, opoids and non-steroidal anti-inflammatory compounds have received attention from scientists working in the area of drug discovery. Morphine and its derivatives have been used classically for the management of pain. As this class is riddled with severe side effects of addiction and respiratory depression, hence the search for new compounds to avoid these side effects, led to the approval of tramadol. Tramadol acts through a combination of weak µ-opoid and mono-analgesic (noradrenaline and serotonin) mechanisms. Further exploitation of synthetic analogues of tramadol for improved dual mechanism targeting treatment of severe nociceptive and neuropathic pain helped in identification of tapentadol. The tapentadol is chemically 3-[(1R,2R')-3-(dimethylamino)-1-ethyl-2-methylpropyl] phenol hydrochloride. Synthesis of tapentadol has been achieved from 1-(3-(benzyloxy)phenyl)propan-1-one or variables of that, through a series of reactions. Chirality is introduced by the use of either auxiliary or resolution. Tapentadol was launched in 2009 for improved analgesic efficacy in chronic and neuropathic pain disorders by a combined agonist activity at µ-opoid receptor with norepinephrine reuptake inhibition. Till date, several procedures on the synthesis and applications for the tapentadol and related compounds/intermediates are reported in literature with varying levels of success and some of them are Patent titled "1-Phenyl-3-dimethylamino-propane derivatives having pharmacological activity" publication number EP0693475 discloses the synthesis of tapentadol via Grignard reaction, chlorination and reduction. Throughout the reaction intermediate salt formation wherever required and final hydrochloride salt preparation is done using trimethylchlorosilane. The drawback of above invention is the use of chiral HPLC column to separate the desired enantiomer and the use of TMSCl for preparation of hydrochloride salt which renders the process industrially uneconomical.

WO2004108658 titled "Process for the preparation of tapentadol" describes process for the preparation of (2R, 3R)-3-(3-methoxyphenyl)-N,N,2-trimethylpentan-1-amine, the penultimate intermediate to prepare tapentadol. The required stereoisomer is separated to get (2R,3R)-3-(3-methoxyphenyl)-N,N,2-trimethylpentan-1-amine which can be treated with concentrated hydrobromic acid to get tapentadol. The drawback of above invention is the formation of mixture of diastereomers in equal ratio thus affecting the economy of the process.

WO2008012046 titled "Preparation of 3-[(1R,2R)-3-(dimethylamino)-1ethyl-2-methylpropyl]phenol" describes another method for the preparation of tapentadol, wherein 1-(3-(benzyloxy)phenyl)propan-1-one is reacted with N-methyl-N-methylene-methaneaminium chloride in presence of acetyl chloride and solvent acetonitrile to obtain compound 1-(3-(benzyloxy)phenyl)-3-(dimethylamino)-2-methylpropan-1-one. The compound is resolved with L-(−)-dibenzoyltartaric acid to get (S)-1-(3-(benzyloxy)phenyl)-3-(dimethylamino)-2-methylpropan-1-one. The isolated compound is then reacted with ethyl magnesium bromide undergoing Grignard reaction to isolate (2S,3R)-3-(3-(benzyloxy)phenyl)-1-(dimethylamino)-2-methylpentan-3-ol, which on reaction with trifluoroacetic anhydride in acetic acid results in acetylated compound. The acetylated compound on hydrogenolysis results in the compound 3-[(2R, 3R)-1-(dimethylamino)-2-methylpentan-3-yl]phenol. The drawback of this invention is the use of costly reagents and solvents like trifluoroacetic anhydride for acetylation and acetonitrile solvent for the condensation reaction affecting economy of the process on industrial scale.

WO2008012047 titled "Process for the preparation of (1R,2R)-3-(3-dimethylamino-1-ethyl-2-methyl-propyl)-phenol" describes yet another method for the preparation of tapentadol, where tapentadol is isolated as hydrochloride salt of tapentadol hydrochloride. The drawback of above invention is the resolution of the racemic intermediate using chiral reagent increases the reaction steps, and cost of the reaction.

Therefore, there remains a need for an improved process for scalable synthesis of 3-[(2R,3R)-1-(dimethylamino)-2-methylpentan-3-yl]phenol that reduces the number of steps, avoids chromatographic separation at every step and employs safe and commercially relevant reagents for the reaction.

The strategies used by most researchers depend on an acyclic approach wherein the Grignard addition of 3-bromoanisole onto ethyl ketone generates diastereomeric mixtures which were carried forward to achieve the target molecule. We reasoned, the Grignard addition of bromoanisole onto a cyclic ketone, which upon opening of the cyclic form would be a preferred option for a better stereo control.

OBJECTIVE OF THE INVENTION

The main objective of the present invention is to provide an efficient process for the preparation of tapentadol and analogs of Formula I in very high yielding multi-step process.

Another objective of the present invention is to provide an efficient process for the preparation of tapentadol and analogs of Formula I, comprising of purification free steps.

Yet another objective of the present invention is to provide an efficient process for the preparation of tapentadol and analogs of Formula I, which is highly feasible and reliable at industrial scale.

SUMMARY OF THE INVENTION

Accordingly, the present invention provides a process for the preparation of tapentadol and analogs or stereoisomers or compounds of formula (I);

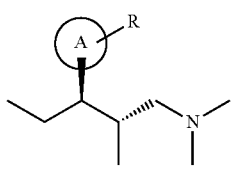

Formula (I)

wherein, A is aryl, heteroaryl, and cycloalkyl;

R is H, OH, $OR^1$, halogen, $C_1$-$C_{12}$ alkyl, cycloalkyl, aryl or heteroaryl;

$R^1$ is $C_1$-$C_{12}$ alkyl, cycloalkyl, aryl or heteroaryl, wherein each of these groups may further be substituted with one or more substituent selected from H, OH, halogen, CN, $NO_2$, $C_1$-$C_4$ alkyl or phenyl;

comprising the steps of:

i) treating tetrahydro-4H-thiopyranone (V) with dimethylamine, to obtain compound of formula (IV),

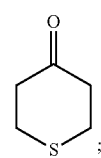

Formula (V)

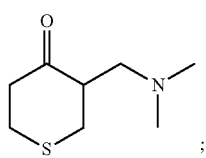

Formula (IV)

ii) reacting compound of formula (IV) as obtained from step i) with magnesium turnings and

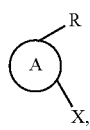

to obtain compound of formula (III);

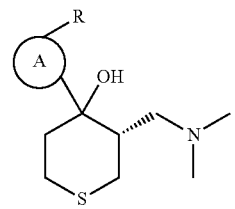

Formula (III)

wherein, A is aryl, heteroaryl, and cycloalkyl;

R is H, OH, $OR^1$, halogen, $C_1$-$C_{12}$ alkyl, cycloalkyl, aryl or heteroaryl;

$R^1$ is $C_1$-$C_{12}$ alkyl, cycloalkyl, aryl or heteroaryl, wherein each of these groups may further be substituted with one or more substituent selected from H, OH, halogen, CN, $NO_2$, $C_1$-$C_4$ alkyl or phenyl; and X is halide;

iii) treating compound of formula (III) as obtained from step ii) with acid followed by a reducing agent in presence of an organic solvent to undergo an dehydroxylation and/or elimination reaction to obtain crude compound of formula (II) as a mixture of compounds of formula (IIa) and (IIb); and

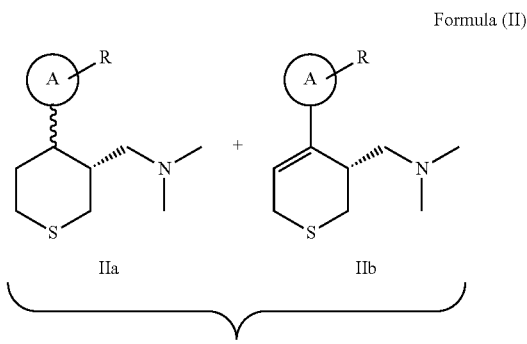

Formula (II)

iv) reducing the crude compound of formula (II) as obtained from step iii) with transition metal containing reducing agent in presence of an alcoholic solvent to undergo sulphur removal, to obtain compound or analog or stereoisomer of formula (I);

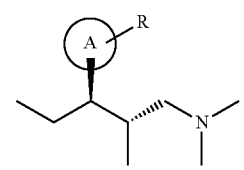

Formula (I)

v) optionally, hydrolysing compound of formula (I), wherein $R=OR^1$ is converted to $R=OH$, by reacting compound of formula (I) with a mineral acid.

In an embodiment of the invention, the acid is selected from a group consisting of trifluoroacetic acid, camphor sulphonic acid, acetic acid, formic acid and hydrochloric acid.

In an embodiment of the invention, the reducing agent is sodium borohydride or lithium aluminum hydride.

In an embodiment of the invention, the organic solvent is selected from dichloromethane, tetrahydrofuran, dimethylsulfoxide, dimethyformamide, dioxin, acetonitrile, ethylacetate, hexane, pentane, toluene, acetone and diethylether.

In an embodiment of the invention, the transition metal containing reducing agent is Raney Ni.

In an embodiment of the invention, the halide is selected from group consisting of bromide and chloride.

In another embodiment of the invention, the alcoholic solvent is selected from a group consisting of ethanol, methanol, propanol and butanol.

In yet another embodiment of the invention, the mineral acid is selected from a group consisting of hydrochloric acid, sulphuric acid, and hydrobromic acid.

In yet another embodiment of the invention, all of the process steps are purification-free steps.

In yet another embodiment of the invention, the final desired anti isomer of compound of formula (I) is obtained in 96.4% HPLC purity.

In yet another embodiment of the present invention, it provides purification-free process steps i.e., no costly purification steps are required.

In another embodiment of the present invention, the process provides two diastereomers of the tapentadol i.e., anti and syn isomer and the ratio of the same is 96.4:3.4.

BRIEF DESCRIPTION OF THE DRAWINGS

FIG. 1: Schematic flowchart for the preparation of analogs of formula (I);

FIG. 2: Schematic flowchart for the synthesis of tapentadol;

FIG. 3: Schematic flowchart for the synthesis of tapentadol along with the reaction conditions.

ABBREVIATIONS

HCHO, Formaldehyde; HNMe$_2$, Dimethylamine; aq., Aqueous; DMSO, Dimethyl Sulfoxide; rt, room temperature; THF, tetrahydrofuran; NaBH$_4$, sodium borohydride; CF$_3$COOH, Trifluoroacetic acid; MeOH, Methyl alcohol; H$_2$, Hydrogen.

DETAILED DESCRIPTION OF THE INVENTION

The present invention provides a highly effective process for the preparation of tapentadol and analogs of formula (I)

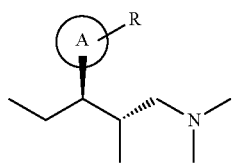

Formula I wherein, A is aryl, heteroaryl, and cycloalkyl; R is H, OH, OR$^1$, halogen, C$_1$-C$_{12}$ alkyl, cycloalkyl, aryl or heteroaryl; R$^1$ is C$_1$-C$_{12}$ alkyl, cycloalkyl, aryl or heteroaryl, wherein each of these groups may further be substituted with one or more substituent selected from H, OH, halogen, CN, NO$_2$, C$_1$-C$_4$ alkyl or phenyl.

Tapentadol is an FDA approved drug for the treatment of moderate to severe acute pain. Its improved analgesic efficacy in chronic and neuropathic pain disorders by a combined agonist activity at µ-opoid receptor with norepinephrine reuptake inhibition.

The present process employs effective and simple chemical reactions to produce tapentadol and analogs or stereoisomers or compounds of formula (I). The individual steps do not require complex purification techniques. The final product is obtained in almost 96.4% purity, and hence the process does not require any purification step. The FIG. 1 shows the general reaction flow chart for synthesis of compounds of formula (I) starting from tetrahydro-4H-thiopyranone (V). The ring A and substituent R in FIG. 1 is as described above.

In view of the FIG. 1, if it is desired to convert R=OR$^1$ to R=OH, an extra step of hydrolysis may be optionally carried out after the reduction step, and at the end of the process.

Compounds of formula (I) thus obtained can be tapentadol or analogs thereof.

In particular, the invention also provides a process for producing tapentadol starting from tetrahydro-4H-thiopyranone (V) as shown in the FIG. 2.

Both the schemes (FIGS. 1 and 2) start with tetrahydro-4H-thiopyranone (V) as the starting material, which is first aminomethylated, followed by Grignard reaction, dehydroxylation and subsequent reduction.

Optionally the last hydrolysis step for the synthesis of tapentadol, in particular is carried out as illustrated in FIG. 2.

Optionally the last hydrolysis step may be employed for any analogs of compound of formula (I) if desired. The final step of hydrolysis is done when it is desired to convert R=OR$^1$ into R=OH. The hydrolysis can be carried out in presence of acids.

The present process can be performed very effectively with feasible reaction parameters such as reaction times, solvents, reagents, temperature, workup, isolation and purification. Further, this process protocol serves as a highly viable strategy which could be most suitable for the industrial scale production of tapentadol and analogs or compounds of Formula (I). This process is also suitable for the generation of a large library of intermediates and analogues of tapentadol.

The first step of this process involves organocatalytic aminomethylation of tetrahydro-4H-thiopyranone (V) in presence of dimethylamine, wherein diverse functionalization is possible with the use of substrate screening methods. The subsequent Michael product (IV) can be utilized to generate yet another library of intermediates (III) upon Grignard reaction using aryl or cycloalkyl or heteroaryl halides of choice, using standard Grignard reaction conditions. Further, dehydroxylation followed by reduction leads to the formation of the key moiety II (a mixture of IIa and IIb). This intermediate when subjected to transition metal mediated reduction conditions undergoes an inherent removal of sulphur from the substrate to produce products of Formula (I). Finally, if it is desired to convert the R=OR$^1$ to R=OH in Compound I, like in the case of tapentadol, then the target compounds could be achieved by acid hydrolysis. All the reaction sequences can be performed by using a variety of substrate partners to generate and build a vast library of tapentadol analogues with diverse functional modifications. All the reaction steps involve purification without the use of column chromatography. Systematic characterization of the individual reaction product was done at each stage of the process. This makes the reaction sequence industrially applicable and scalable.

The present process for the preparation of tapentadol and analogs and intermediates as illustrated in the FIGS. 1 and 2 are described as follows. This process is the most convenient and simple method of a reaction sequence that employs simple key starting materials and reaction parameters comprising of following steps:

i) The first step of the process is aminomethylation reaction (Michael reaction) of tetrahydro-4H-thiopyranone (V) by treating it with dimethylamine, to give compounds of formula IV.

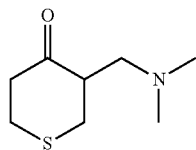

IV ii) The second step in the process is Grignard reaction of the product of Michael reaction (IV) by reacting it with magnesium turnings and aryl or cyclic or heteroaryl halides, to obtain compounds of formula III.

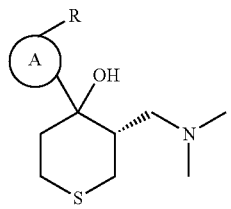

III iii) The third step is dehydroxylation and/or elimination reaction by treating compound of formula (III) as obtained the product of step ii with acid like trifluoroacetic acid and then react with a reducing agent like sodium borohydride in presence of an organic solvent to undergo an dehydroxylation and/or elimination reaction to obtain compounds of formula IIa and IIb as a mixture, collectively called compound II, Formula II

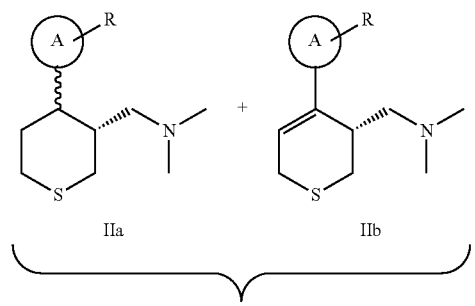

IIa    IIb wherein, A is selected from aryl, heteroaryl, and cycloalkyl;
R is H, OH, $OR^1$, halogen, $C_1$-$C_{12}$ alkyl, cycloalkyl, aryl or heteroaryl;
$R^1$ is $C_1$-$C_{12}$ alkyl, cycloalkyl, aryl or heteroaryl, wherein each of these groups may further be substituted with one or more substituent selected from H, OH, halogen, CN, $NO_2$, $C_1$-$C_4$ alkyl or phenyl.

The acid can be organic or inorganic acids for example trifluoroacetic acid, camphor sulphonic acid, acetic acid, formic acid, hydrochloric acid etc. The organic solvent is selected from dichloromethane, tetrahydrofuran, dimethylsulfoxide, dimethyformamide, dioxin, acetonitrile, ethylacetate, hexane, pentane, toluene, acetone and diethylether.

iv) The fourth step of the process is transition metal mediated reduction and in-built one pot sulphur removal of II as obtained the product of step iii with transition metal containing reducing agent in presence of an alcoholic solvent to undergo sulphur removal, to obtain compounds of formula I. with transition metal containing reducing agent mentioned is Raney Ni. The alcoholic solvent is selected from a group consisting of ethanol, methanol, propanol and butanol.

Optionally, v) The fifth step of the process involves hydrolysis with a mineral acid to convert the R=$OR^1$ to R=OH in Compound I give compounds of formula I.

Formula (I)

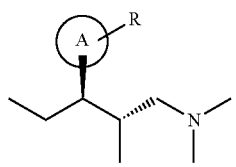

wherein, A is selected from aryl, heteroaryl, and cycloalkyl; R is H, OH, $OR^1$, halogen, $C_1$-$C_{12}$ alkyl, cycloalkyl, aryl or heteroaryl; $R^1$ is $C_1$-$C_{12}$ alkyl, cycloalkyl, aryl or heteroaryl, wherein each of these groups may further be substituted with one or more substituent selected from H, OH, halogen, CN, $NO_2$, $C_1$-$C_4$ alkyl or phenyl.

The mineral acid in the optional step v is selected from a group consisting of hydrochloric acid, sulphuric acid, and hydrobromic acid.

The most important aspect of this invention is the absence of any purification step in the entire process. Yet, the desired stereoisomer (anti) is obtained in 96.4% purity. This makes this process a highly commercial and economical process.

In this process, all the reaction steps were monitored by thin layer chromatography and the crude products obtained were subjected to purification using extraction or filtration to get the pure compounds in good yields. If required, crystallization can also be used for purifying the reaction intermediates. Further, all the resultant compounds/products were systematically characterized using various analytical and spectral methods.

EXAMPLES

Following examples are given by way of illustration and therefore should not be construed to limit the scope of the invention. All compounds and reagents unless specifically stated have been purchased commercially from commercial vendors. The main starting compound of tetrahydro-4H-thiopyranone (V) was purchased from Beijing Yibai Biotechnology Co. Ltd., China (Mainland).

Example 1: 3-((Dimethylamino)Methyl) Tetrahydro-4H-Thiopyran-4-One (IV)

To a stirred solution of tetrahydro-4H-thiopyranone (V) (100 mg, 0.860 mmol) in 0.047 mL of formaldehyde (36% aq. solution, 0.430 mmol), in 0.062 mL of dimethylamine (40% aq. solution, 0.470 mmol) in 1.0 mL of DMSO was added. The reaction was quenched with 0.5 mL of 2N HCl. The pH of the solution was adjusted to 2 with HCl to make the hydrochloride salt. The aqueous reaction mixture was treated with ethyl acetate. The product was extracted into water and the remaining organic impurities were removed by giving ethyl acetate washings. The hydrochloride salt was basified to a pH 9 using 2N NaOH and extracted into ethyl acetate. The organic layers were now dried and evaporated. The solvent was removed under reduced pressure gave compound of formula IV as a brownish oil 114 mg (77%). $^1$H NMR (500 MHz, CDCl$_3$) δ 3.17 (dd, J=13.4, 4.3 Hz, 1H), 2.91-2.97 (m, 3H), 2.88-2.81 (m, 1H), 2.78-2.73 (m, 1H), 2.71-2.66 (m, 2H), 2.43-2.37 (m, 1H), 2.21 (s, 6H); $^{13}$C NMR (101 MHz, CDCl$_3$) δ 210.0, 58.8, 51.0, 45.8, 43.6, 34.5, 31.1; IR (neat) $\upsilon_{max}$ 2940, 2822, 2771, 1701, 1458, 1262, 1038, 850; HRMS (ESI) calcd for C$_8$H$_{16}$NOS [M+H]$^+$: 174.0953; found: 174.0951.

Example 1 was scaled up, and the various different combinations and weights of other reactants are mentioned in Table 1 below. The product (IV) obtained in Examples 2, 3 and 4 had similar NMR ($^1$H and $^{13}$C), IR, HRMS data as in Example 1.

TABLE 1

Representing Examples 2, 3 and 4

| Example No. | Starting material* (V) wt (g)/mmol | 36% Aq. Formaldehyde/ mL | 40% aq. Dimethylamine/ mL | DMSO/mL | Product* (IV)/g | Yield** % |
|---|---|---|---|---|---|---|
| 2 | 0.5 g/4.30 mmol | 0.24 mL | 0.32 mL | 5 mL | 0.38 g | 76 |
| 3 | 50 g/430 mmol | 23.7 mL | 31.5 mL | 500 mL | 37 g | 75 |
| 4 | 100 g/860 mmol | 48 mL | 63 mL | 1200 mL | 74 g | 76 |

*Note:
Starting material (V) is tetrahydro-4H-thiopyranone
Product (IV) is 3-((dimethylamino)methyl)tetrahydro-4H-thiopyran-4-one
**Yield based on starting material recovery.

Example 5: 3-((Dimethylamino)Methyl)-4-(3-Methoxyphenyl)Tetrahydro-2H-Thiopyran-4-ol (III)

To a stirred solution of Mg turnings (55.4 mg, 2.3 mmol) in 3.0 mL of dry THF was added slowly 3-bromoanisole (281 mg, 1.5 mmol) dissolved in 2.0 mL of dry THF under argon in a flame dried two necked round bottom flask equipped with a reflux condenser. Heat is generated in such reactions. The reaction was carefully observed for 5 minutes and allowed to cool for 1 h. The Grignard reagent thus prepared was slowly added to the 3-((dimethylamino) methyl)tetrahydro-4H-thiopyran-4-one (IV) (200 mg, 1.15 mmol) in 2.0 mL of THF dropwise using cannula at 0° C. The stirring was continued for 12 h at room temperature. Saturated ammonium chloride was added to the reaction mixture slowly at 0° C. and the product 3-((dimethylamino) methyl)-4-(3-methoxyphenyl) tetrahydro-2H-thiopyran-4-ol (III) was obtained by extraction with ethyl acetate (269 mg, 83%) as a yellow oil (a single diastereomer.). $^1$H NMR (500 MHz, CDCl$_3$) δ 7.28-7.26 (m, 0.5H), 7.26-7.24 (m, 0.5H), 7.16-7.03 (m, 2H), 6.77 (dd, J=8.1, 1.8 Hz, 1H), 3.82 (s, 3H), 3.53 (t, J=12.7 Hz, 1H), 3.24 (td, J=13.6, 2.9 Hz, 1H), 2.47 (dd, J=14.0, 4.4 Hz, 1H), 2.40-2.34 (m, 2H), 2.27-2.20 (m, 2H), 2.08 (s, 6H), 2.03-1.94 (m, 2H); $^{13}$C NMR (126 MHz, CDCl$_3$) δ 159.8, 151.1, 129.4, 117.3, 111.9, 110.8, 76.2, 62.1, 55.4, 47.9, 46.1, 42.7, 29.4, 24.9; IR (neat) $\upsilon_{max}$ 3420, 2923, 2832, 1593, 1471, 1429, 1256, 1042, 925, 756, 698; HRMS (ESI) calcd for C$_{15}$H$_{24}$NO$_2$S [M+H]$^+$: 282.1528; found: 282.152.

Example 5 was scaled up, and the various different combinations and weights of other reactants are mentioned in Table 2 below. The product (III) obtained in Examples 6, 7 and 8 had similar NMR ($^1$H and $^{13}$C), IR, HRMS data as in Example 5.

TABLE 2

Representing Examples 6, 7 and 8

| Example No. | Mg turnings/g | THF for Mg turnings/mL | 3-bromoanisole/ mL | THF for 3-bromoanisole/ mL | Starting material* (IV) wt (g)/mmol | THF for (IV)/mL | Product* (III)/g | Yield % |
|---|---|---|---|---|---|---|---|---|
| 6 | 6.93 | 250 mL | 23.6 | 150 mL | 25 g/144 mmol | 150 mL | 33.2 | 82 |
| 7 | 8.3 | 350 mL | 28.3 | 200 mL | 30 g/173 mmol | 200 mL | 40 | 82 |
| 8 | 12.2 | 500 mL | 41.5 | 250 mL | 44 g/254 mmol | 250 mL | 58.2 | 82 |

*Note:
Starting material (IV) is 3-((dimethylamino)methyl)tetrahydro-4H-thiopyran-4-one
Product (III) is 3-((dimethylamino)methyl)-4-(3-methoxyphenyl)tetrahydro-2H-thiopyran-4-ol.

Example 9: 1-(4-(3-Methoxyphenyl) Tetrahydro-2H-Thiopyran-3-Yl)-N,N-Dimethyl Methanamine (II)

To a stirred solution of trifluoroacetic acid (TFA) (1 mL) under inert conditions was added NaBH$_4$ (201 mg, 5.3 mol) slowly at 0° C. followed by a solution of 3-((dimethylamino)methyl)-4-(3-methoxyphenyl)tetrahydro-2H-thiopyran-4-ol (III) (100 mg, 0.3 mmol) in CH$_2$Cl$_2$ (2 mL) was added to the reaction mixture at the same temperature. The reaction mixture was allowed to stir for 6 hours at ambient temperature. After completion, reaction mixture was poured into ice water (6 mL) and was saturated Na$_2$CO$_3$ solution was added to quench the acid. The reaction mixture was extracted with CH$_2$Cl$_2$ (2×2 mL, then 1×1 mL), dried and evaporated to give mixture of products (IIa and IIb) as light brown oil, 76.5 g (81.3%) which was used directly for next reaction without any further purification.

Example 9 was scaled up, and the various different combinations and weights of other reactants are mentioned in Table 3 below.

TABLE 3

Representing Examples 10 and 11

| Example No. | TFA/mL | NaBH$_4$/g | Starting material* (III) wt (g)/mmol | DCM for starting material/ mL | Ice water/ mL | Yield % |
|---|---|---|---|---|---|---|
| 10 | 50 mL | 41 g | 20 g/71.1 mmol | 150 mL | 150 mL | 81% |
| 11 | 100 mL | 91 g | 45 g/160 mmmol | 250 mL | 600 mL | 81% |

*Note:
Starting material (III) is 3-((dimethylamino)methyl)-4-(3-methoxyphenyl)tetrahydro-2H-thiopyran-4-ol;
Product (II) is 1-(4-(3-methoxyphenyl) tetrahydro-2H-thiopyran-yl)-N,N-dimethylmethanamine obtained as IIa and IIb in a 70:30 ratio.

Example 12: 3-(3-methoxyphenyl)-N,N-2-trimethyl pentan-1-amine (I)

The crude product 1-(4-(3-methoxyphenyl)tetrahydro-2H-thiopyran-3-yl)-N,N-dimethylmethanamine (5 g, 18.8 mmol) (II) was dissolved in 50 ml of methanol, treated with a suspension of excess Raney Ni (20 g) and heated to 80° C. The reaction mixture was allowed to reflux for 15 h under vigorous stirring. The reaction was allowed to settle and the supernatant removed via pipette and filtered through a plug of celite. Additional methanol was added to the reaction vial and stirred for 5 min before again being allowed to settle and the supernatant removed. This process was repeated for additional two times. The combined filtrates concentrated to give 3-(3-methoxyphenyl)-N,N,2-trimethyl pentan-1-amine (I) (3.45 g, 78%) as yellow oil (96.4%, in favor of desired anti diastereomer). $^1$H NMR (300 MHz, CDCl$_3$) δ 7.23-7.13 (m, 1H), 6.79-6.66 (m, 3H), 3.80 (s, 3H), 2.63-2.24 (m, 2H), 2.19 (s, 2H), 2.12 (s, 4H), 2.01-1.82 (m, 2H), 1.76-1.51 (m, 2H), 0.95 (d, J=6.5 Hz, 2H), 0.82-0.67 (m, 4H); $^{13}$C NMR (101 MHz, CDCl$_3$) δ 159.5, 159.2, 146.4, 144.5, 129.0, 128.6, 121.9, 121.1, 115.4, 114.7, 110.9, 110.7, 65.2, 65.0, 55.2, 51.6, 49.9, 46.0, 36.8, 35.6, 26.1, 24.1, 16.0, 14.9, 12.7, 12.5; IR (neat) υ$_{max}$ 3171, 2943, 2825, 1593, 1461, 1250, 1040, 780, 706; HRMS (ESI) calcd for C$_{15}$H$_{26}$NO [M+H]$^+$: 236.2014; found: 236.2011.

Example 12 was scaled up, and the various different combinations and weights of other reactants are mentioned in Table 4 below. The product (II) obtained in Examples 13 and 14 had similar NMR ($^1$H and $^{13}$C), IR, HRMS data as in Example 12.

TABLE 4

Representing Examples 13 and 14

| Example No. | Starting material* (II) Wt (g)/mmol | Methanol for (III)/mL | Raney Ni/g | Product* (I)/g | Yield % |
|---|---|---|---|---|---|
| 13 | 30 g/106 mmol | 300 | 120 g | 20.2 | 76 |
| 14 | 55 g/195.7 mol | 500 | 200 g | 38 | 78 |

*Note:
Starting material (II) is 1-(4-(3-methoxyphenyl) tetrahydro-2H-thiopyran-3- yl)-N,N-dimethyl methanamine used as a mixture of IIa and IIb; Product (I) is 3-(3-methoxyphenyl)-N,N,2-trimethyl pentan-1-amine.

Example 15: 3-(1-(Dimethylamino)-2-Methylpentan-3-Yl) Phenol (or Tapentadol)

A mixture of 3-(3-methoxyphenyl)-N,N-2-trimethylpentan-1-amine, from Examples 12, 13 or 14 (1 g, 4.2 mmol) and aqueous hydrobromic acid (HBr) (46%, 20 ml) was heated under stirring at 100-110° C. for 3 h. The reaction mixture was then cooled to room temperature. The reaction mixture was neutralized with sodium bicarbonate. Resulting product was extracted with ethyl acetate. The organic layer was washed with water and dried over anhydrous sodium sulphate and concentrated to give 3-(1-(dimethylamino)-2-methylpentan-3-yl) phenol (I) (921 mg, 98%) as a brownish oil. In HPLC analysis anti and syn diastereomers were found to be 96.4:3.4 ratio i.e. 96.4% purity of the desired anti diastereoisomer was obtained, as measured using HPLC.

NMR data for anti diastereomer, $^1$H NMR (500 MHz, CDCl$_3$) δ 7.12 (t, J=7.8 Hz, 1H), 6.68-6.61 (m, 2H), 6.58 (s, 1H), 2.33-2.27 (m, 1H), 2.17 (s, 6H), 2.15-2.10 (m, 1H), 2.09-2.00 (m, 1H), 1.90-1.83 (m, 1H), 1.78-1.68 (m, 1H), 1.60-1.49 (m, 1H), 0.96 (d, J=6.7 Hz, 3H), 0.70 (t, J=7.3 Hz, 3H); $^{13}$C NMR (101 MHz, CDCl$_3$) δ 156.5, 146.1, 129.2, 120.3, 115.8, 113.3, 64.8, 51.5, 45.7, 36.6, 23.9, 16.2, 12.4; IR (neat) υ$_{max}$ 3391, 2958, 2871, 1695, 1464, 1266, 1029, 775; HRMS (ESI) calcd for C$_{14}$H$_{24}$NO [M+H]$^+$: 222.1858; found: 222.1865.

NMR data for syn diastereomer, $^1$H NMR (400 MHz, CDCl$_3$) δ 7.10 (t, J=7.8 Hz, 1H), 6.65 (dd, J=8.0, 2.1 Hz, 2H), 6.59-6.55 (m, 1H), 2.46-2.37 (m, 1H), 2.29-2.25 (m, 1H), 2.24 (s, 6H), 2.02-1.94 (m, 1H), 1.94-1.82 (m, 1H), 1.78-1.58 (m, 2H), 0.80-0.71 (m, 6H); $^{13}$C NMR (101 MHz, CDCl$_3$) δ 156.2, 144.6, 128.9, 121.4, 116.0, 113.4, 77.5, 77.2, 76.8, 65.4, 50.7, 45.9, 35.8, 26.8, 15.6, 12.7; IR (neat) υ$_{max}$ 3310, 2951, 2865, 1595, 1465, 1263, 1028, 779; HRMS (ESI) calcd for C$_{14}$H$_{24}$NO [M+H]$^+$: 222.1858; found: 222.1878.

Example 15 was scaled up, and the various different combinations and weights of other reactants are mentioned in Table 5 below. The product (I) obtained in Examples 16 and 17 had similar NMR ($^1$H and $^{13}$C), IR, HRMS data as in Example 13; for both the diastereomers.

TABLE 5

Representing Examples 16 and 17

| Example No. | Starting material* (I) Wt (g)/mmol | Aq HBr (46%)/mL | Product* (Tapentadol)/g | Yield % |
|---|---|---|---|---|
| 16 | 9 g/3.8 mmol | 100 mL | 8.2 | 97 |
| 17 | 25 g/106 mmol | 250 mL | 22.8 | 97 |

*Note:
Starting material (I) 3-(3-methoxyphenyl)-N,N,2-trimethylpentan-1-amine
Product (tapentadol) is 3-(3-methoxyphenyl)-N,N-2-trimethylpentan-1-amine Anti & syn diastereomers in each of the above examples were separated by using short column chromatography (silica gel 60-120, neutralized with triethylamine) using EtOAc/Hexane (1:9) as mobile phase. Pure desired anti diastereoisomer was isolated in similar yields.

Advantages of the Invention

The various advantages of the present process are given below.
1. The present process serves as a highly efficient and scalable production method for the preparation of tapentadol, an FDA approved drug for the treatment of moderate to severe acute pain, an analgesic agent.
2. Isolation and/or purification of the product/s is/are straight forward and no column chromatography involved.
3. This is an attractive and economic method for the production of tapentadol and analogs.
4. This process could be adopted to generate a large library of process intermediates and tapentadol analogues at industrial scale.
5. In the nutshell, this invention provides a process for preparation of tapentadol and analogs or stereoisomers or compounds of formula (I) by purification free process steps which renders the process more reliable, cost effective, more preferable and efficient on industrial scale production

We claim:
1. A process for the preparation of tapentadol compounds of formula (I);

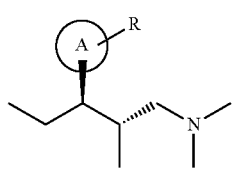

Formula (I)

wherein, A is aryl, heteroaryl, and cycloalkyl;
R is H, OH, OR1, halogen, C1-C12 alkyl, cycloalkyl, aryl or heteroaryl;
R1 is C1-C12 alkyl, cycloalkyl, aryl or heteroaryl, wherein each of these groups may further be substituted with one or more substituent selected from H, OH, halogen, CN, NO2, C1-C4 alkyl or phenyl;

comprising the steps of:
i) treating tetrahydro-4H-thiopyranone (V) with 40% aqueous solution of dimethylamine and 36% aqueous solution of formaldehyde, to obtain compound of formula (IV),

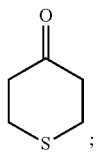

Formula (V)

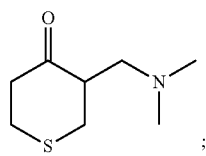

Formula (IV)

ii) reacting compound of formula (IV) as obtained from step i) with magnesium turnings and

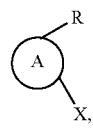

to obtain compound of formula (III);

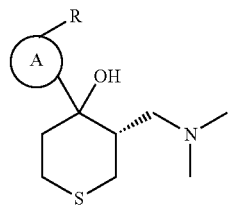

Formula (III)

wherein, A is aryl, heteroaryl, and cycloalkyl;
R is H, OH, OR$^1$, halogen, C$_1$-C$_{12}$ alkyl, cycloalkyl, aryl or heteroaryl;
R$^1$ is C$_1$-C$_{12}$ alkyl, cycloalkyl, aryl or heteroaryl, wherein each of these groups may further be substituted with one or more substituent selected from H, OH, halogen, CN, NO$_2$, C$_1$-C$_4$ alkyl or phenyl; and
X is halide;
iii) treating compound of formula (III) as obtained from step ii) with acid followed by a reducing agent in presence of an organic solvent to undergo an dehydroxylation and/or elimination reaction to obtain crude compound of formula (II) as a mixture of compounds of formula (IIa) and (IIb); and

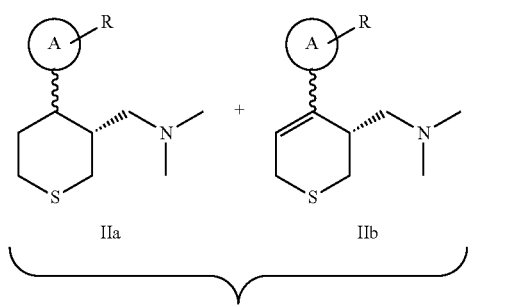

Formula (II)

iv) reducing the crude compound of formula (II) as obtained from step iii) with transition metal containing reducing agent in presence of an alcoholic solvent to undergo sulphur removal, to obtain compound of formula (I);

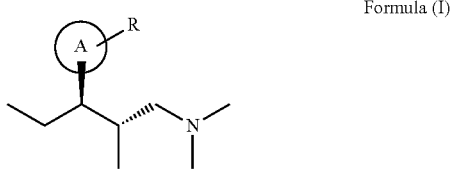

Formula (I)

v) optionally, hydrolysing compound of formula (I), wherein R=$OR^1$ is converted to R=OH, by reacting compound of formula (I) with a mineral acid;

wherein the steps (i) to (iv) are purification free steps.

2. The process according to claim 1, wherein the acid is selected from a group consisting of trifluoroacetic acid, camphor sulphonic acid, acetic acid, formic acid and hydrochloric acid.

3. The process according to claim 1, wherein the reducing agent is sodium borohydride or lithium aluminum hydride.

4. The process according to claim 1, wherein the organic solvent is selected from dichloromethane, tetrahydrofuran, dimethylsulfoxide, dimethyformamide, dioxin, acetonitrile, ethylacetate, hexane, pentane, toluene, acetone and diethylether.

5. The process according to claim 1, wherein the transition metal containing reducing agent is Raney Ni.

6. The process according to claim 1, wherein the halide is selected from group consisting of bromide and chloride.

7. The process according to claim 1, wherein the alcoholic solvent is selected from a group consisting of ethanol, methanol, propanol and butanol.

8. The process according to claim 1, wherein the mineral acid is selected from a group consisting of hydrochloric acid, sulphuric acid, and hydrobromic acid.

9. The process according to claim 1, wherein all of process steps are purification-free steps.

10. The process according to claim 1, wherein the final desired anti isomer of compound of formula (I) is obtained in 96.4% HPLC purity.

* * * * *